(12) United States Patent
Kong et al.

(10) Patent No.: US 8,685,648 B2
(45) Date of Patent: Apr. 1, 2014

(54) ENDONUCLEASE-ENHANCED HELICASE-DEPENDENT AMPLIFICATION

(75) Inventors: Huimin Kong, Wenham, MA (US); Yanhong Tong, Boxford, MA (US)

(73) Assignee: BioHelix Corporation, Beverly, MA (US)

( * ) Notice: Subject to any disclaimer, the term of this patent is extended or adjusted under 35 U.S.C. 154(b) by 19 days.

(21) Appl. No.: 13/146,602

(22) PCT Filed: Feb. 3, 2010

(86) PCT No.: PCT/US2010/023089
§ 371 (c)(1),
(2), (4) Date: Oct. 7, 2011

(87) PCT Pub. No.: WO2010/091111
PCT Pub. Date: Aug. 12, 2010

(65) Prior Publication Data
US 2012/0040359 A1   Feb. 16, 2012

Related U.S. Application Data

(60) Provisional application No. 61/149,390, filed on Feb. 3, 2009.

(51) Int. Cl.
*C12Q 1/68* (2006.01)

(52) U.S. Cl.
USPC .......................................... 435/6.12

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 5,322,770 A | 6/1994 | Gelfand | |
| 5,455,166 A | 10/1995 | Walker | |
| 5,470,723 A | 11/1995 | Walker et al. | |
| 5,494,810 A | 2/1996 | Barany et al. | |
| 5,624,833 A | 4/1997 | Gelfand et al. | |
| 5,714,320 A | 2/1998 | Kool | |
| 5,869,251 A | 2/1999 | Schuster et al. | |
| 5,916,779 A | 6/1999 | Pearson et al. | |
| 6,214,587 B1 | 4/2001 | Dattagupta et al. | |
| 6,235,502 B1 | 5/2001 | Weissman et al. | |
| 6,306,588 B1 | 10/2001 | Solus et al. | |
| 6,555,349 B1 | 4/2003 | O'Donnell | |
| 6,794,177 B2 | 9/2004 | Markau et al. | |
| 6,977,148 B2 | 12/2005 | Dean et al. | |
| 7,282,328 B2 * | 10/2007 | Kong et al. | 435/6.12 |
| 7,662,594 B2 * | 2/2010 | Kong et al. | 435/91.2 |
| 7,829,284 B2 * | 11/2010 | Kong et al. | 435/6.12 |
| 2003/0138800 A1 * | 7/2003 | Van Ness et al. | 435/6 |
| 2003/0219792 A1 | 11/2003 | Armes et al. | |
| 2005/0069926 A1 | 3/2005 | Cole et al. | |
| 2006/0094052 A1 * | 5/2006 | Kelman et al. | 435/6 |

FOREIGN PATENT DOCUMENTS

| | | |
|---|---|---|
| WO | WO 00/41524 A2 | 7/2000 |
| WO | WO 01/09347 A2 | 2/2001 |
| WO | WO 2004/027025 A2 | 4/2004 |
| WO | WO 2010/091111 A1 | 8/2010 |

OTHER PUBLICATIONS

Dong et al. (A coupled complex of T4 DNA replication helicase (gp41) and polymerase (gp43) can perform rapid and processive DNA strand-displacement synthesis, Proc. Natl. Acad. Sci. USA, vol. 93, pp. 14456-14461, Dec. 1996).*
Tong et al. (Development of isothermal TaqMan assays for detection of biothreat organisms, BioTechniques 45:543-557, Nov. 2008).*
Ward et al. (Restriction Endonuclease-Mediated Selective Polymerase Chain Reaction, American Journal of Pathology, vol. 153, No. 2, Aug. 1998).*
Robinson et al. (Restriction Endonucleases, in Molecular Biology Problem Solver: A Laboratory Guide, Ed. Alan S. Gerstein, Ch. 9, 2001).*
Invitrogen.*
Ali et al., "An oligomeric form of *E. coli* UvrD is required for optimal helicase activity", J. Mol. Biol., vol. 293, No. 4, pp. 815-834 (1999).
An et al., "Characterization of a thermostable UvrD helicase and its participation in helicase-dependent amplification", J. Biol. Chem., vol. 280, No. 32, pp. 28952-28958 (2005).
Barany, "Genetic disease detection and DNA amplification using cloned thermostable ligase", Proc. Natl. Acad. Sci. USA, vol. 88, No. 1, pp. 189-193 (1991).
Bernstein and Richardson, Purification of the 56-kDa component of the bacteriophage T7 primase/helicase and characterization of its nucleoside 5'-triphosphatase activity, J. Biol. Chem., vol. 263, No. 29, pp. 14891-14899 (1988).
Caruthers and McKay, "Helicase structure and mechanism", Curr. Opin. Struct. Biol., vol. 12. No. 1, pp. 123-133 (2002).
Cline et al., "PCR fidelity of pfu DNA polymerase and other thermostable DNA polymerases", Nucl. Acids Res., vol. 24, No. 18, pp. 3546-3551 (1996).
Dillingham et al., "RecBCD enzyme is a bipolar DNA helicase", Nature, vol. 423, No. 6942, pp. 893-897 (2003).
Dong et al., "A coupled complex of T4 DNA replication helicase (gp41) and polymerase (gp43) can perform rapid and processive DNA strand-displacement synthesis", Proc. Natl. Acad. Sci. USA, pp. 93, No. 25. pp. 14456-14461 (1996).
Fire and Xu, "Rolling replication of short DNA circles", Proc. Natl. Acad. Sci. USA, vol. 92, No. 10, pp. 4641-4645 (1995).
Guatelli et al., "Isothermal, in vitro amplification of nucleic acids by a multienzyme reaction modeled after retroviral replication", Proc. Natl. Acad. Sci. USA, vol. 87, No. 5, pp. 1874-1878 (1990).

(Continued)

*Primary Examiner* — Christopher M Babic
*Assistant Examiner* — Aaron Priest
(74) *Attorney, Agent, or Firm* — McDermott Will & Emery LLP (57) ABSTRACT

The invention provides methods and compositions for enhancing the speed and sensitivity of helicase-dependent amplification through the use of an endonuclease.

18 Claims, 4 Drawing Sheets

(56) References Cited

OTHER PUBLICATIONS

Harmon and Kowalczykowski, "Biochemical characterization of the DNA helicase activity of the *Escherichia coli* RecQ helicase", J. Biol. Chem., vol. 276, No. 1, pp. 232-243 (2001).

International Search Report from related PCT Patent Application No. PCT/US2010/023089 mailed Apr. 13, 2010, application now published as International Publication No. WO2010/091111 on Aug. 12, 2010.

Kaplan and Steitz, "DnaB from *Thermus aquaticus* unwinds forked duplex DNA with an asymmetric tail length dependence", J. Biol. Chem., vol. 274, No. 11, pp. 6889-6897 (1999).

Keohavong and Thilly, "Fidelity of DNA polymerases in DNA amplification", Proc. Natl. Acad. Sci. USA, vol. 86, No. 23, pp. 9253-9257 (1989).

Kim et al., "Interactions of gene 2.5 protein and DNA polymerase of bacteriophage T7", J. Biol. Chem., vol. 267, No. 21, pp. 15032-15040 (1992).

Lechner and Richardson, "A preformed, topologically stable replication fork. Characterization of leading strand DNA synthesis catalyzed by T7 DNA polymerase and T7 gene 4 protein", J. Biol. Chem., vol. 258, No. 18, pp. 11185-11196 (1983).

Matson, "*Escherichia coli* helicase II (urvD gene product) translocates unidirectionally in a 3' to 5' direction", J. Biol. Chem., vol. 261, No. 22, pp. 10169-10175 (1986).

Roman and Kowalczykowski, "Characterization of the helicase activity of the *Escherichia coli* RecBCD enzyme using a novel helicase assay", Biochemistry, vol. 28, No. 7, pp. 2863-2873 (1989).

Runyon and Lohman, "*Escherichia coli* helicase II (uvrD) protein can completely unwind fully duplex linear and nicked circular DNA", J. Biol. Chem., vol. 264, No. 29, pp. 17502-17512 (1989).

Runyon et al., "*Escherichia coli* helicase II (UvrD) protein initiates DNA unwinding at nicks and blunt ends", Proc. Natl. Acad. Sci. USA, vol. 87, No. 16, pp. 6383-6337 (1990).

Taylor and Smith, "RecBCD enzyme is a DNA helicase with fast and slow motors of opposite polarity", Nature, vol. 423, No. 6942, pp. 889-893 (2003).

Tong et al., "Development of isothermal TaqMan assays for detection of biothreat organisms", Biotechniques, vol. 45, No. 5, pp. 543-557 (2008).

Vincent et al., "Helicase-dependent isothermal DNA amplification", Embo Rep., vol. 5, No. 8, pp. 795-800 (2004).

Walker et al., "Isothermal in vitro amplification of DNA by a restriction enzyme/DNA polymerase system", Proc. Natl. Acad. Sci. USA, vol. 89, No. 1, pp. 392-396 (1992).

Yamaguchi et al., "MutS and MutL activate DNA helicase II in a mismatch-dependent manner", J. Biol. Chem., vol. 273, No. 15, pp. 9197-9201 (1998).

\* cited by examiner

ENDONUCLEASE-ENHANCED HELICASE-DEPENDENT AMPLIFICATION

RELATED APPLICATION

This application is a national stage filing under 35 U.S.C. 371 of PCT/US2010/023089, filed Feb. 3, 2010, which claims the benefit of U.S. Application No. 61/149,390, filed Feb. 3, 2009.

FIELD

The present invention relates to methods and compositions to improve the speed and sensitivity of helicase-dependent amplification.

BACKGROUND

Nucleic acid amplification has been widely used for research and molecular diagnostics. PCR (polymerase chain reaction) is a traditional method for nucleic acid amplification which requires thermocycling. Heat denaturation during PCR thermocycling is a powerful and important step to uniformly separate DNA duplexes, generating single-stranded templates for subsequent primer annealing. Several platforms exist for isothermal amplification, including SDA (strand displacement amplification), TMA (transcription-mediated amplification), RCA (rolling cycle amplification), LAMP (loop-mediated amplification), NASBA (nucleic acid sequence-based amplification), and HDA (helicase-dependent amplification). HDA is different from other isothermal technologies because the HDA technology employs a helicase to separate the double-stranded nucleic acid. It is desirable to improve the speed and sensitivity of nucleic acid amplification technologies with high speed and high sensitivity, particularly for use in research and diagnostic applications.

Several methods have been developed to improve speed and sensitivity for PCR. Some of the methods that can improve PCR performance have also been successful for improving HDA performance. However, HDA is different from PCR, as HDA can be performed isothermally and relies on a helicase to separate the strands of double-stranded nucleic acids. Several specific methods have been applied to improve HDA. For example, previous studies have found that the protein concentrations of DNA polymerase and helicase can be optimized to improve the performance of HDA. Although increasing amounts of enzymes (helicases and DNA polymerases) can increase detection speed, the Limit-of-Detection (LoD), the minimum number of target nucleic acids required for reliable detection, generally remains unchanged at, for example, 5-50 copies.

HDA uses helicase(s) to separate a DNA duplex. Helicase is not a sequence-specific protein and therefore does not specifically recognize a target region. The efficiency of the helicase separating the double-stranded nucleic acid, especially in the target region specified by forward and reverse primers, is therefore a rate-limiting factor. Based on the unwinding direction, helicases can be grouped into two major types: the 3'-5' helicases and the 5'-3' helicases. The well-studied *E. coli* UvrD helicase unwinds DNA in a 3' to 5' direction (Matson, S. W. *J. Biol. Chem.*, 261, 10169-10175. (1986)). Some helicases can unwind duplex nucleic acid from blunt ends; advantages of using such helicases are described in U.S. Pat. No. 7,282,328. Other helicases require a single-stranded "tail" on the substrate duplex, generally a 3' tail for 3'-5' helicases and a 5' tail for the 5'-3' enzymes.

SUMMARY OF THE INVENTION

The present invention is based, in part, on the discovery that the speed and sensitivity of helicase-dependent amplification can be improved through the use of an endonuclease, such as a restriction endonuclease. The extraction and purification of nucleic acid substrates typically shears or nicks them, generating randomly-distributed accessible ends for a helicase to load onto the duplex. Perhaps as a result, the art has not previously appreciated any need for or benefit from introducing additional free ends in a target for helicase-dependent amplification. Surprisingly, the inventors have now discovered that treating the target nucleic acid with an endonuclease can significantly improve both the sensitivity and speed of helicase-dependent amplification.

Accordingly, in one aspect the invention provides an improved composition for helicase-dependent amplification. The composition includes a helicase, a DNA polymerase, at least one primer, and an endonuclease. The endonuclease can be a restriction endonuclease, such as a Type II or Type IIs restriction endonuclease. Exemplary endonucleases include AvaII, BanII, AseI, SspI, SpeI, MboI, MboII, SwaI, BsrI, BtsCI, CviQI, CviAII, Tsp45I, Fnu4HI, MsII, MspAII, SacII, AgeI, DraI, and XmnI. The helicase is preferably thermostable. The composition can include additional components, such as deoxynucleotides, buffer, magnesium, sodium, one or more additional primers, and/or single stranded binding proteins, for example.

The invention also provides methods for assaying a sample by combining a composition like those described above with a sample containing or potentially containing a nucleic acid that hybridizes to one or more primers in the composition. In this way, the presence or absence of the target nucleic acid can be detected, the amount of a target nucleic acid can be measured, or a target nucleic acid known to be present can be amplified to facilitate its subsequent characterization (e.g. determining the presence or absence of a genetic variation) or other use. For example, the sample can be a biological sample from a subject and can include human tissue, cells or body fluid (e.g. blood, serum, plasma, lymph, urine, sweat, tears, semen, vaginal fluid, nipple aspirate, sputum, ejaculate, saliva, bronchial lavage, pleural effusion, peritoneal fluid, amniotic fluid, glandular fluid, fine needle aspirates, spinal fluid, conjunctival fluid, or cerebrospinal fluid), and the target nucleic acid can be a human nucleic acid or a foreign nucleic acid from a virus, bacterium, fungus, parasite, etc.). Alternatively, the sample could be an environmental, animal or industrial sample. In one embodiment, the sample contains no more than 1 ng of DNA (e.g. no more than 0.1 ng or no more than 0.01 ng). In some embodiments, the sample contains no more than about 300 copies of the target nucleic acid (e.g. no more than about 30 copies or no more than about 3 copies).

The invention also provides methods for amplifying a nucleic acid by treating the nucleic acid with an endonuclease and amplifying the treated nucleic acid in a helicase-dependent amplification reaction. The amplification can follow the treatment step, or the two processes can be concurrent. The endonuclease can be a restriction endonuclease such as a Type II or a Type IIs restriction endonuclease. Exemplary endonucleases include AvaII, BanII, AseI, SspI, SpeI, MboI, MboII, SwaI, BsrI, BtsCI, CviQI, CviAII, Tsp45I, Fnu4HI, MsII, MspAII, SacII, AgeI, DraI, and XmnI. In one embodiment, the helicase-dependent amplification reaction includes a helicase (preferably thermostable), a DNA polymerase, a buffer, deoxynucleotides, magnesium, and at least one primer.

In each of the various methods of practicing the invention, the endonuclease preferably, but not necessarily, cleaves the nucleic acid within 5 kb (and perhaps within 500 bp) of the nucleotide sequence in the nucleic acid that hybridizes to the primer (i.e. the primer binding site).

Additional aspects and advantages of the invention will be apparent from the following description of certain particular embodiments of the invention.

BRIEF DESCRIPTION OF THE DRAWINGS

FIG. 1 shows amplification from 50,000 copies plasmid DNA. Ct (the threshold cycle, defined as the cycle number at which the fluorescence level has exceeded the detection threshold) is 14 for the assays without SspI, but is reduced to around 11.5 for the assays with SspI. FIG. 2 shows amplification from 20 ng human genomic DNA; Ct is around 14 for the assays with or without SspI.

FIG. 3 shows the effects of SpeI. Ct is 14 for the assays without SspI, and is reduces to around 11.5 for the assays with SspI. FIG. 4 shows the effects of BanII: Ct is 13 for the assays without BanII, and is reduced to about 11 with BanII.

DETAILED DESCRIPTION OF SPECIFIC EMBODIMENTS

The invention improves the sensitivity of, and accelerates, helicase-dependent amplification through the use of endonucleases. Restriction endonucleases, nicking endonucleases, and homing endonucleases recognize and cleave specific nucleic acid sequences, generating 5'ss ends, 3'ss ends or blunt ends. More than 3,000 restriction endonucleases with over two hundred different specificities have been isolated from bacteria (Roberts and Macelis, Nucleic Acids Res. 26:338-350 (1998)). Type II restriction endonucleases are the most commonly used restriction enzymes for molecular biology applications: they cut DNA at defined positions close to or within their recognition sequences. They produce discrete restriction fragments and distinct gel banding patterns and are the only class of restriction enzyme commonly used in the laboratory for DNA analysis and gene cloning. Examples of type II enzymes include EcoRI, HindIII, SspI, and BanII, each cleaving DNA within its recognition sequence. The next most common Type II enzymes, usually referred to as 'type IIs,' are those such as FokI and AlwI that cleave outside of their recognition sequence to one side. During an HDA reaction, the selected restriction endonucleases generate break points (or ends) of the nucleic acid substrates that are near a target region. These resulting ends recruit helicases to the adjacent target region and thus increase the chance or frequency of the helicase unwinding a target region.

In an embodiment, an endonuclease is used prior to an HDA reaction (separate from the HDA reaction, in a two-step format). In such a two-step format, restriction endonucleases digest the DNA targets first at the optimal working temperature, typically in an HDA reaction buffer or in a buffer that does not inhibit the following HDA reaction. The digested nucleic acid substrates can then be used in the subsequent HDA reaction. In another embodiment, the endonuclease is used together with an HDA enzyme mix (in a one-step format, generally including a helicase, a DNA polymerase, and optionally single-stranded DNA binding proteins). In such a one-step format, the reaction speed of the endonucleases should be fast enough to generate a certain number of specific ends during the time of reaction set-up (including, if applicable, the time of adding the master reaction mix to each sample in the individual tube, mixing, and bringing the sample to an incubator which has already been set to the HDA reaction temperature). In general, the set-up time may be in the range of about 2 to about 15 minutes, depending on how many samples are to be tested. As an illustrative example, the "time-saver qualified enzymes" from New England BioLabs Inc, (NEB, Ipswich, Mass.) provide restriction endonucleases with fast reaction speeds. This group of fast endonucleases digest about 1 μg of DNA in about 5 minutes using about 1 μl of enzyme under recommended conditions. The one-step format is easier to perform as there is no additional step required to add the restriction endonucleases. On the other hand, fewer restriction endonucleases are as suitable for the one-step format because it requires fast speed and high digestion efficiency. In general, an enzyme that is suitable for the one-step format can always be used in a two-step reaction.

Several preferred restriction endonucleases for use in the present invention are selected on the basis of one or more the following factor(s):

Fast reaction speed. If the endonucleases are used together with an HDA enzyme mix, reaction speed is an important factor in the improvement in amplification. The "time-saver qualified enzymes" from NEB are good choices, for example. However, if the endonucleases are used separately in a two-step reaction, reaction speed need not be an issue.

The buffer for endonuclease cleavage is preferably compatible with HDA reaction buffer: the enzyme's activity is not inhibited by the reaction buffer used for HDA.

The endonuclease does not or is not known to recognize, bind or cleave within the target sequence to be amplified. If the target sequence is cleaved by a restriction enzyme, the truncated target region can no longer be used as a template for amplification.

The endonuclease does not recognize, bind or cut the corresponding internal control sequence, if an internal control is included in the HDA reaction.

Proximity of the cleavage site to the target region. Ideally, the cleavage site can be within 5,000 bp of the target region. More preferably, the cleavage site is only 1-500 bp away from the target region.

To improve reaction performance without cleaving the target sequence, the sequence in the region for restriction enzyme digestion and HDA amplification should be relatively conserved. Highly polymorphic regions of a target nucleic acid are preferably avoided.

The cleavage frequency of an endonuclease is determined, in part, by the number of base pairs it recognizes. Some restriction endonucleases recognize 6 base pairs. For example, the restriction endonuclease SspI recognizes AATATT and cleaves in the middle. As another example, restriction endonuclease SpeI recognizes ACTAGT and cleaves between A and C. In general, restriction endonucleases that recognize longer sequences (less frequent cutters such as SspI and SpeI) show more enhancement in most of the HDA reactions. The high-frequency cutters (for example, those that recognize 4 base pairs) will not only generate restriction ends close to the targets, but also generate more ends in the entire nucleic acid substrates. Since all ends will recruit helicases, higher numbers of available ends in the nucleic acid substrates may compete with ends that are adjacent to the specific target sequence. This "dilution" effect can reduce the effectiveness of the restriction enzyme in enhancing HDA.

In an embodiment, the restriction endonucleases are enzymes which digest the DNA at a lower temperature during reaction setup (for example, from about 0° C. to about 37° C.).

In an embodiment, the improvement effects of the endonucleases depend on the amount of DNA. In a sample having very low amounts of the initial targets, for example 1-50 copies of DNA (for example, plasmid DNA, bacteria or virus genomic DNA, or human genomic DNA), endonuclease cleavage can greatly improve the chance of helicases binding to the limited number of targets, and make the reaction more consistent at low target concentrations. When an HDA reaction with low-initial-target is evaluated in real-time, the Ct (the threshold cycle, defined as the cycle number at which the fluorescence level has exceeded the detection threshold) is reduced if an endonuclease is used. This indicates that the HDA speed is enhanced by the restriction enzyme, evidenced by the earlier appearance of the fluorescent signal across the Ct line. In addition, the success rate of the HDA reaction with low-initial-target is improved by using appropriate endonucleases: the standard deviation of Ct is reduced. Restriction endonucleases also reduce primer dimer formation (caused by non-specific primer annealing and amplification) at low target concentrations. In a sample having a medium amount of the input targets, for example, more than 50 copies of DNA, endonuclease cleavage still improves the detection speed. If the experiment is evaluated by real-time assay, the time needed to see a positive fluorescent signal across the Ct line is reduced by about 2 to about 6 minutes. On the other hand, in HDA reactions with very high amounts of input substrate, for example, about 20 ng of human genomic DNA, there will be an overwhelming number of non-specific ends, exceeding the number of helicases. In this case, no significant enhancement effects by the restriction endonucleases are observed.

In an embodiment, a mixture of one or more compatible endonucleases for use with the corresponding HDA can be selected. For example, an endonuclease which can cleave the upstream sequence of the target can be combined with an endonuclease which can cleave the downstream sequence of the target.

In an embodiment, the use of restriction endonucleases in an HDA reaction is compatible with other methods to improve HDA performance. For example, the methods include, but are not limited to, protein engineering or modification to improve the function of the protein (helicases, polymerases, other accessory proteins).

The following experimental examples are provided to illustrate certain embodiments of the invention, but are not intended to limit the invention.

EXAMPLES

Example 1

Use of Endonucleases to Improve Reaction Speed of HDA

In this example, a method is disclosed to improve HDA reaction speed by restriction endonuclease cleavage. The target of amplification was within *Homo sapiens* breast cancer 1 (Genbank accession No. NT_010755 REGION: 4967748..4971174, 3427 bp). This region was cloned into pCR-Blunt II-TOPO (Invitrogen, Carlsbad, Calif.), named as pBRCA-TOPO. Specific primers BRCA2F (AGCTTAG-CAGGAGTCCTAGCCCTTT) (SEQ ID NO: 1) and BRCA2R (TCTGAGGACTCTAATTTCTTGGCCC) (SEQ ID NO: 2), were used to amplify an 85 bp fragment from this region. In order to compare the effects of endonuclease cleavage from a medium amount of DNA and a high amount of DNA (with overwhelming numbers of ends), the same endonuclease was tested with different targets: plasmid DNA (50,000 copies of pBRCA-TOPO, around 0.38 pg) vs. human genomic DNA (20 ng, around 6000 copies). 20 ng of human genomic DNA contain many more ends than 0.38 pg of plasmid DNA.

The restriction endonuclease SspI (New England BioLabs, Inc, Ipswich, Mass.) was chosen to show the effects of enzyme cleavage, which can cleave the sequence around 187 bp downstream of the specific amplification region. The target sequence of the enzyme is AAT↓ATT. After cleavage, blunt ends are generated. The HDA reaction was performed first by combining the following components to produce a reaction master mix with a final volume of 45 µl/reaction (make 4× reaction master mix for 2 tested samples):

5 µl 10× Annealing buffer II (see below*)
0.75 µl 5.0 µM BRCA2F primer (SEQ ID NO: 1)
0.75 µl 5.0 µM BRCA2R primer (SEQ ID NO: 2)
2.0 µl 100 mM $MgSO_4$
2.0 µl 500 mM NaCl
2.0 µl 10 mM dNTP
1.5 µl 100 mM dATP
0.5 µl EvaGreen (20×, Biotium, Hayward, Calif.)
1 µl ROX dye (50×, Invitrogen, Carlsbad, Calif.)
3.5 µl IsoAmpII enzyme mix (BioHelix, Beverly, Mass.)
1 µl SspI or $H_2O$ (for the control without endonuclease) add $dH_2O$ to total 45 µl.

*10× Annealing buffer II contains 100 mM KCl and 200 mM Tris-HCl (pH 8.8 at 25° C.)

For the test with plasmid DNA, in 4 individual PCR reaction tubes, 5 µl of 10,000 copies/µl pBRCA-TOPO was added to each tube. 45 µl of reaction master mix with SspI was added to 2 of the tubes, and 45 µl of reaction master mix without SspI was added to the other two tubes. The reactions were mixed by pipetting up and down several times and then covered with mineral oil. The reaction mixture was immediately incubated in an ABI7300 real-time PCR machine with the well inspector setting: reporter dye: SYBR; quencher: none; passive reference dye: ROX. An ABI7300 real-time PCR instrument was used to monitor the HDA reaction in real-time because no isothermal real-time fluorescent instrument was commercially available. To perform an isothermal reaction on an ABI7300 real-time PCR instrument, which requires a minimum of 1 degree of temperature variation between different cycles, the following program was used:

Stage 1: (30×)
    Step 1: 64.5° C. for 0:05
    Step 2: 63.5° C. for 1:55
    Data collection and real-time analysis enabled
Stage 2: (1×)
Dissociation Stage
    Melt curve data collection and analysis enabled For the test with human genomics DNA, a similar procedure was performed. The only difference was that in 4 individual PCR reaction tubes, 5 µl of 4 ng/µl human genomic DNA (Promega, Madison, Wis.) were added to each tube.

Figure 1:
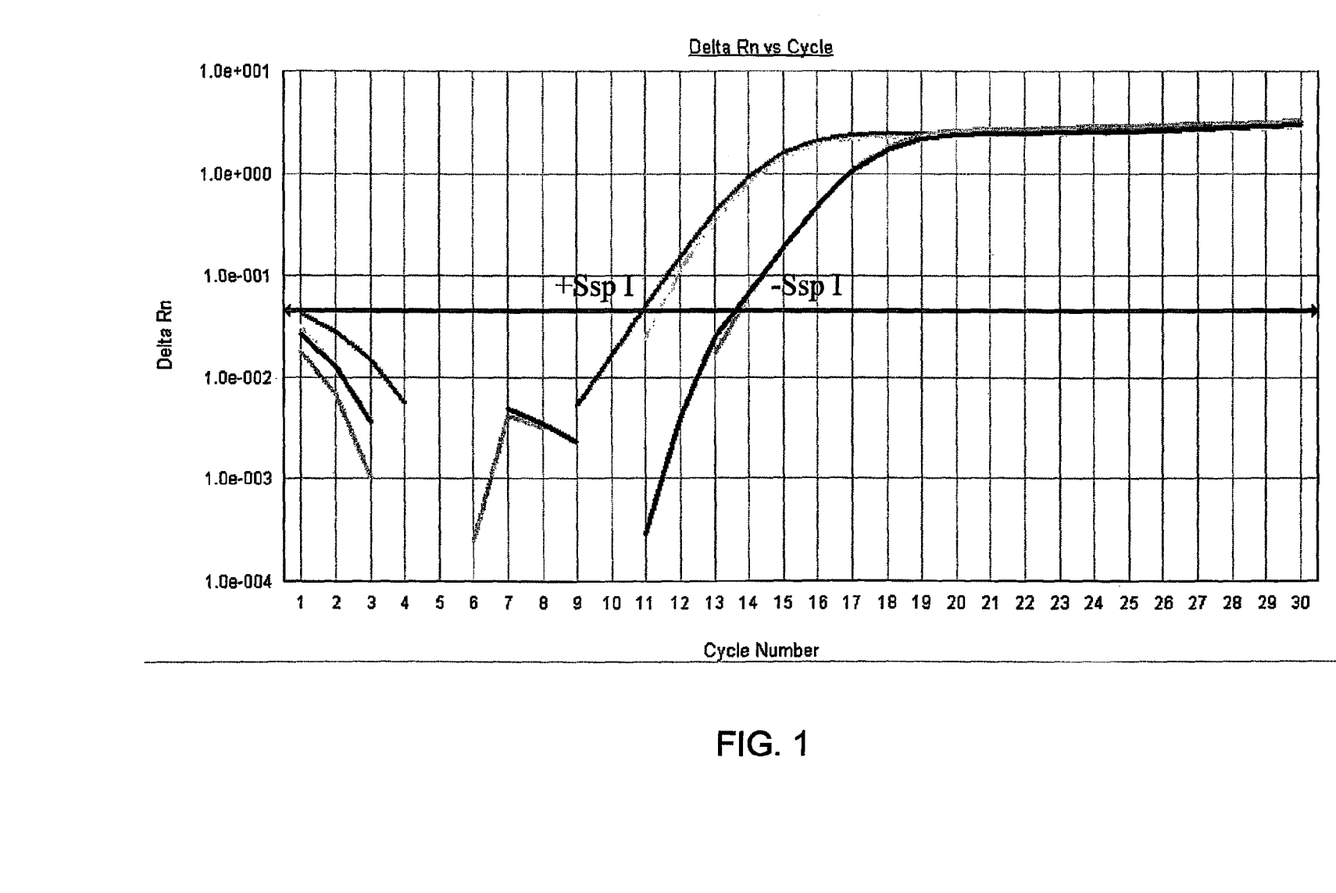
FIG. 1 and FIG. 2 are graphs showing the effects of restriction endonuclease SspI on helicase-dependent amplification from 50,000 copies of plasmid DNA (FIG. 1) or from 20 ng human genomic DNA (FIG. 2) for a one hour amplification at 63.5° C.
Figure 2:
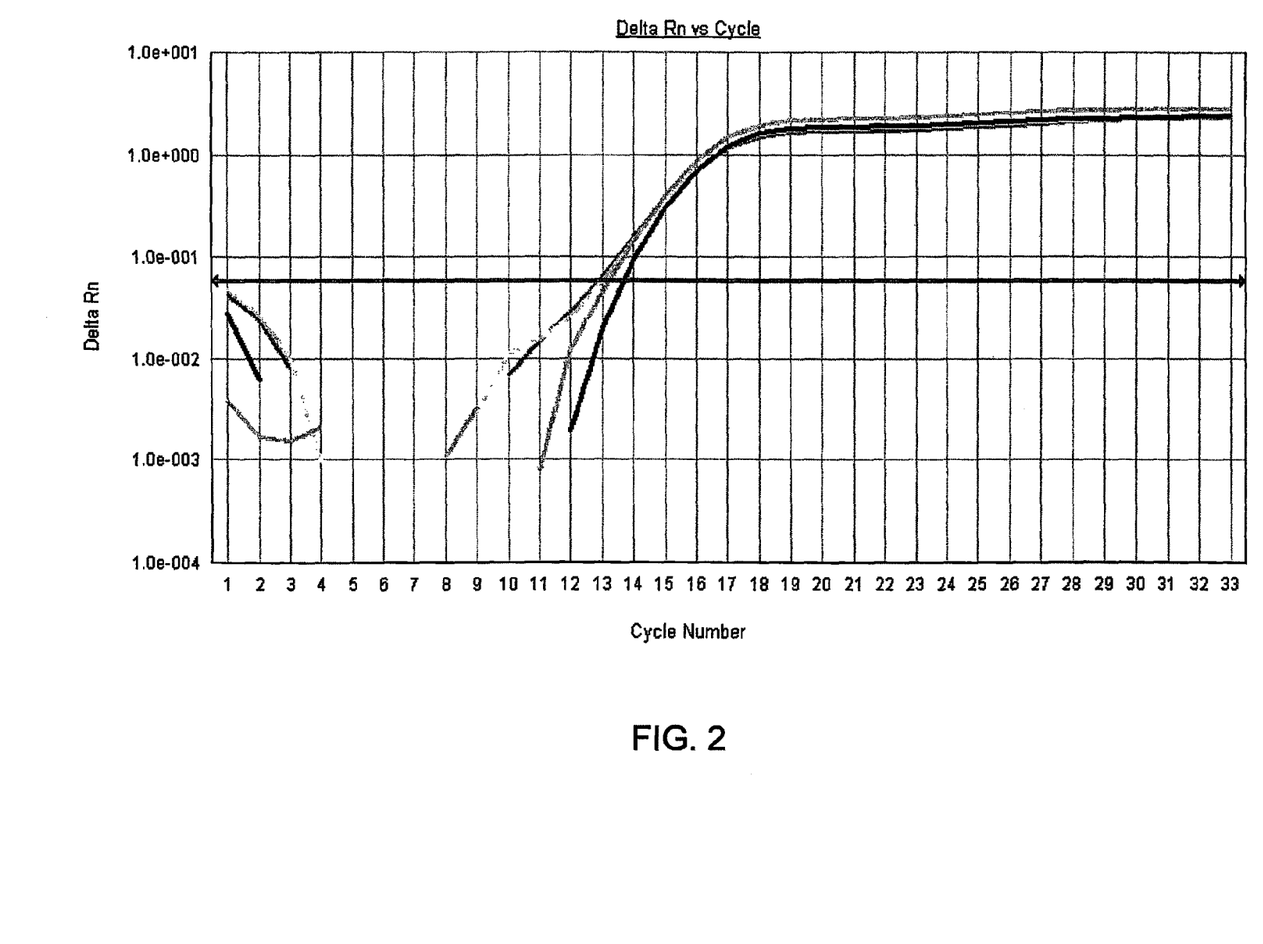

The graphs in FIG. 1 and FIG. 2 were generated by the software of the ABI7300 realtime PCR System as log view of delta Rn versus cycle. When 0.38-pg of plasmid DNA were used in the reactions (FIG. 1), the Ct number was reduced by about 2.5 cycles from around Ct 14 to 11.5 (corresponding to a reduction of amplification time by 5 minutes) in the reaction with SspI compared to the reaction without SspI. However, when 20 ng of human genomic DNA were used in the tests (FIG. 2), there was no obvious difference comparing the reactions with or without SspI. These results demonstrate that in the presence of a high amount of DNA (with an overwhelming number of ends for helicase loading), no significant enhancement to the speed of the HDA reaction was observed.

Example 2

Use of Endonucleases to Improve Detection Sensitivity of HDA when the Target Copy Number is Low In this example, endonuclease cleavage was used to improve the sensitivity of HDA detection. The same target (human genomic DNA) and primers were used as in Example 1 and the same components of the reaction master mix were prepared.

For the assay with SspI endonuclease, 12× reaction master mix with SspI was prepared for 10 samples (same components as described in Example 1). For the assay without SspI, 12× reaction master mix without SspI was prepared for 10 samples. In 20 individual PCR reaction tubes, 5 μl of the following samples were added to each tube:
1-2: 0.2 ng/μl human genomic DNA (around 300 copies per reaction);
3-8: 2 pg/μl human genomic DNA (around 3 copies per reaction);
9-10: $H_2O$ (negative control);
11-12: 0.2 ng/μl human genomic DNA (around 300 copies per reaction);
13-18: 2 pg/μl human genomic DNA (around 3 copies per reaction);
19-20: $H_2O$ (negative control).

Then, 45 μl of reaction master mix with SspI were added to tubes 1-10, and 45 μl of reaction master mix without SspI were added to tubes 11-20. The reactions were mixed by pipetting up and down several times and then covered with mineral oil. The reaction mixture was immediately incubated in an ABI7300 real-time PCR machine with the same program as in Example 1. The results are given in Table 1 below.

TABLE 1

Comparison of SspI effects from the amplification of low copy number of human genomic DNA.

| | Ct from 1 ng DNA (300 copies) | Ct from 0.01 ng DNA (3 copies) | Success rate from 0.01 ng DNA |
|---|---|---|---|
| + SspI | 14.62 ± 0.08 | 18.36 ± 1.08 | 100% (6/6 positive) |
| − SspI | 16.16 ± 0.04 | 22.87 | 16.67% (2/6 fail, 3/6 dimmer) |

For a medium copy number of targets (300 copies of human genomic DNA), the Ct was decreased by about 1.5 cycles (from Ct 16.1 to Ct 14.5) by the endonuclease. For a low copy number of targets (3 copies of human genomic DNA), without the help of SspI, only 1 out of 6 reactions was successful (success rate around 17%). Two reactions failed and 3 reactions generated primer dimers. However, with the help of SspI, the success rate was 100% (6 out of 6 worked), with a standard deviation of Ct of about 1 Ct. This demonstrates that the robustness and sensitivity of the assay has been significantly improved by endonuclease cleavage.

Example 3

Use of Endonucleases Generating a 5' End or a 3' End to Improve the Reaction Speed of HDA In this example, a method is disclosed to improve HDA reaction speed by endonucleases digestion which can generate 5' ends or 3' ends. The same plasmid target pBRCA-TOPO was used as in Example 1 (50,000 copies for each reaction). The target sequence of SpeI is A↓CTAGT; the closest site to the amplification region is around 66 bp upstream of the primer binding site. Upon cleavage, 5' ends are generated. The target sequence of BanII is GRGCY↓C (R represents A or G, Y represents C or T), the closest site to the amplification region is around 387 bp upstream of the primer binding site. Upon cleavage, 3' ends are generated.

The similar reaction master mix was prepared as Example 1. 4× reaction master mix were prepared for 2 tested samples (45 μl/reaction):

5 μl 10× Annealing buffer II (see below*)

0.75 μl 5.0 μM BRCA2F primer (SEQ ID NO:1)

0.75 μl 5.0 μM BRCA2R primer (SEQ ID NO:2)

2.0 μl 100 mM $MgSO_4$ 2.0 μl 500 mM NaCl 2.0 μl 10 mM dNTP 1.5 μl 100 mM dATP 0.5 μl EvaGreen (20×, Biotium, Hayward, Calif.)

1 μl ROX dye (50×, Invitrogen, Carlsbad, Calif.)

3.5 μl IsoAmpII enzyme mix (BioHelix, Beverly, Mass.)

1 μl SpeI, or BanII or $H_2O$ (for the control without endonuclease) add $dH_2O$ to total 45 μl.

For the test with SpeI, in 4 individual PCR reaction tubes, 5 μl of 10,000 copies/μl pBRCA-TOPO were added to each tube. 45 μl of reaction master mix with SpeI were added to 2 of the tubes, and 45 μl of reaction master mix without SpeI were added to 2 of the other tubes. The reactions were mixed well by pipetting up and down several times and then covered with mineral oil. The reaction mixture was immediately incubated in an ABI7300 real-time PCR machine with the same program as Example 1.

A similar procedure was performed with BanII.

Figure 3:
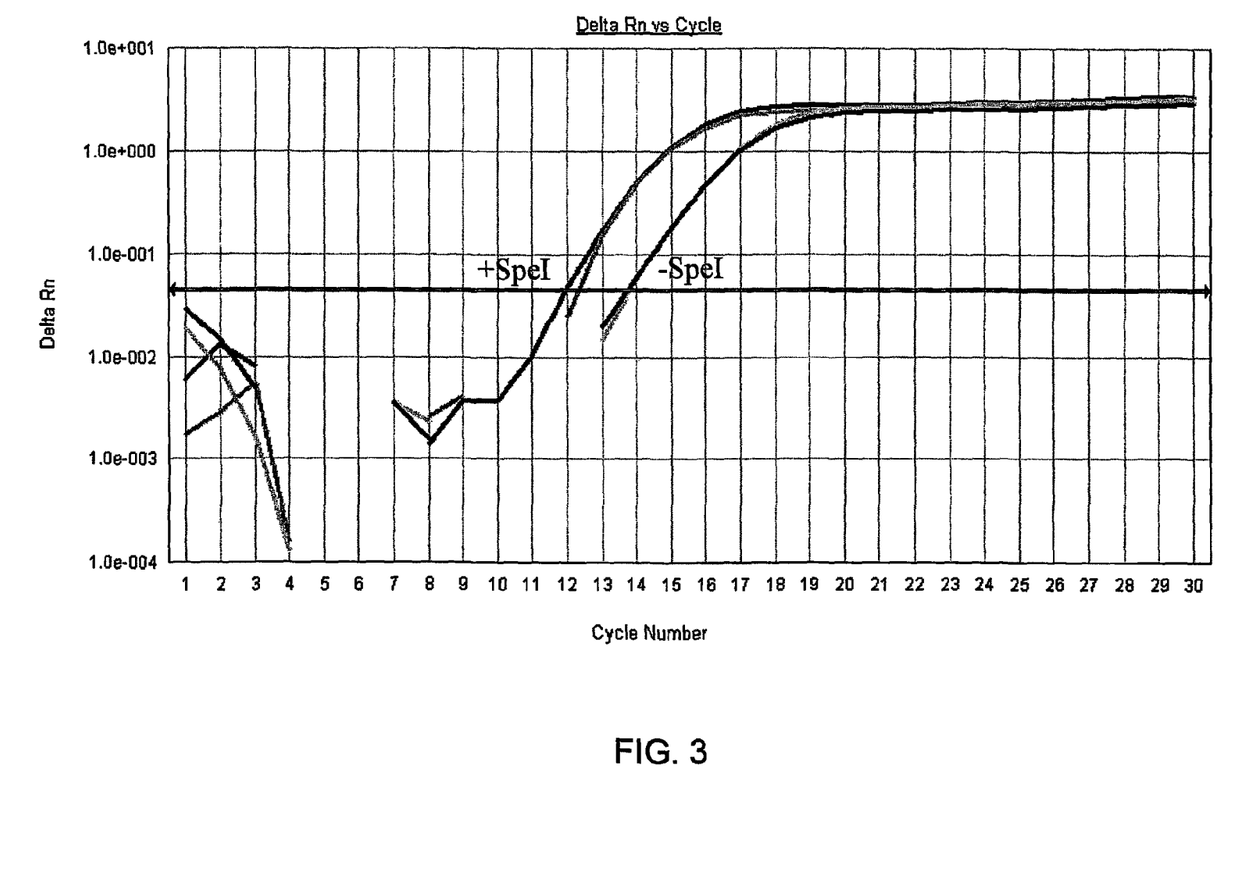
FIG. 3 and FIG. 4 are graphs showing the effects of restriction endonucleases SpeI (FIG. 3) and BanII (FIG. 4) (generating 5' or 3' ends after cleavage, respectively) on helicase-dependent amplification from 50,000 copies of plasmid DNA with a one hour amplification at 63.5° C.
Figure 4:
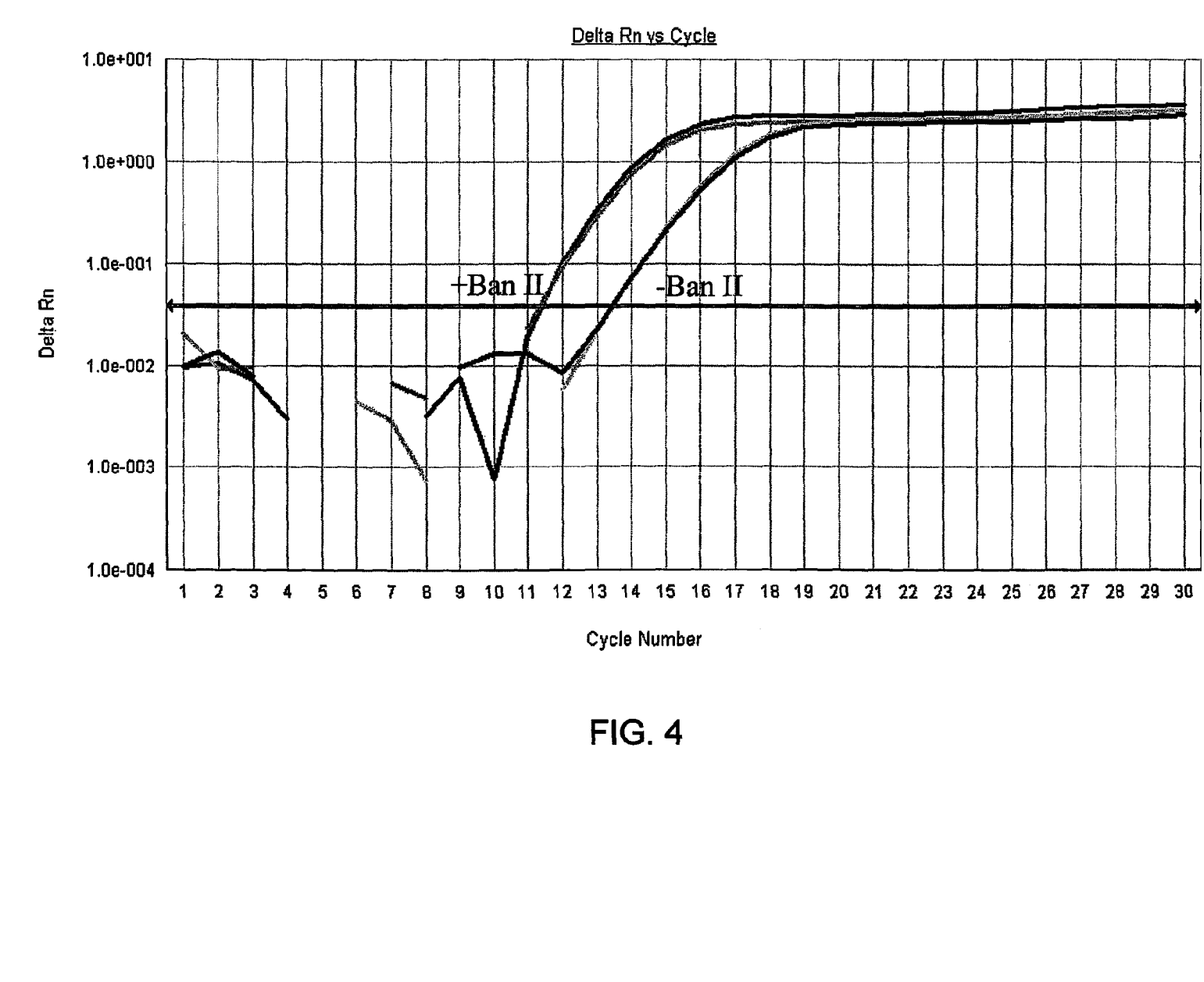

The graphs in FIG. 3 and FIG. 4 were generated by the software of the ABI7300 realtime PCR System. The Ct was reduced by about 2 cycles (corresponding to 4 minutes, from around Ct 14 to 12) in the reaction with SpeI compared to the reaction without SpeI. The Ct was also reduced by about 2 cycles (corresponding to 4 minutes, from around Ct 13 to 11) in the reaction with BanII compared to the reaction without BanII. (The corresponding melt cure analysis is not shown here.) This demonstrates that the HDA reaction speed can be improved by the endonucleases that can generate either 5' ends or 3' ends, or blunt ends as Example 1.

It will be appreciated that several of the above-disclosed and other features and functions, or alternatives thereof, may be desirably combined into many other different systems or applications.

We claim:

1. A method for assaying a sample, the method comprising combining a composition comprising a restriction endonuclease, a helicase, a DNA polymerase, and at least a first primer and a second primer,
   with a sample containing or potentially containing a nucleic acid that hybridizes to the first and second primer, and
   amplifying the target sequence to generate an amplification product
   wherein the restriction endonuclease is one which cannot recognize or cleave the amplification product.

2. The method of claim 1, wherein the sample is a biological sample from a subject.

3. The method of claim 1, wherein the sample comprises human tissue, cells or body fluid.

4. The method of claim 1, wherein the sample is an environmental, animal or industrial sample.

5. The method of claim 1, wherein the sample comprises no more than 1 ng of DNA.

6. The method of claim 5, wherein the sample comprises no more than 0.01 ng of DNA.

7. The method of claim 1, wherein the sample comprises no more than about 300 copies of the nucleic acid that hybridizes to the first and second primer.

8. The method of claim 7, wherein the sample comprises no more than about 3 copies of the nucleic acid that hybridizes to the first and second primer.

9. A method for amplifying a nucleic acid, the method comprising the steps of:
   (a) treating the nucleic acid with a restriction endonuclease,
   (b) incubating the nucleic acid with at least a first primer and a second primer and amplifying the nucleic acid in a helicase-dependent amplification reaction to generate the amplified product, wherein the amplified product is not cleaved by the restriction endonuclease.

10. The method of claim 9, wherein step (a) is performed prior to step (b).

11. The method of claim 9, wherein steps (a) and (b) are performed simultaneously.

12. The method of claim 9, wherein the restriction endonuclease is a Type II restriction endonuclease.

13. The method of claim 9, wherein the restriction endonuclease is a Type IIs restriction endonuclease.

14. The method of claim 9, wherein the restriction endonuclease is AvaII, BanII, AseI, SspI, SpeI, MboI, MboII, SwaI, BsrI, BtsCI, CviQI, CviAII, Tsp45I, Fnu4HI, MsII, MspAII, SacII, AgeI, DraI, or XmnI.

15. The method of claim 9, wherein the helicase-dependent amplification reaction comprises a helicase, a DNA polymerase, a buffer, deoxynucleotides, magnesium, and at least the first and second primer.

16. The method of claim 15, wherein the helicase is a thermostable helicase.

17. The method of claim 1, wherein the restriction endonuclease cleaves the nucleic acid within 5 kb of a sequence that hybridizes to the first and/or second primer.

18. The method of claim 17, wherein the restriction endonuclease cleaves the nucleic acid within 500 bb of a sequence that hybridizes to the first and/or second primer.

* * * * *

UNITED STATES PATENT AND TRADEMARK OFFICE
CERTIFICATE OF CORRECTION

PATENT NO. : 8,685,648 B2  
APPLICATION NO. : 13/146602  
DATED : April 1, 2014  
INVENTOR(S) : Huimin Kong et al.

Page 1 of 1

It is certified that error appears in the above-identified patent and that said Letters Patent is hereby corrected as shown below:

In The Claims

Claim 18, Column 10, line 52: change "within 500 bb" to --within 500 bp--

Signed and Sealed this
Fourteenth Day of June, 2016

Michelle K. Lee
*Director of the United States Patent and Trademark Office*

SEQUENCE LISTING

<160> NUMBER OF SEQ ID NOS: 2

<210> SEQ ID NO 1
<211> LENGTH: 25
<212> TYPE: DNA
<213> ORGANISM: Homo sapiens

<400> SEQUENCE: 1
agcttagcag gagtcctagc ccttt                                       25

<210> SEQ ID NO 2
<211> LENGTH: 25
<212> TYPE: DNA
<213> ORGANISM: Homo sapiens

<400> SEQUENCE: 2
tctgaggact ctaatttctt ggccc                                       25